(12) United States Patent
Kim

(10) Patent No.: US 7,059,851 B2
(45) Date of Patent: Jun. 13, 2006

(54) DENTAL MODEL ARTICULATOR

(76) Inventor: Dae-Woong Kim, 101-19, Hyundai Hometown Apt., Gwiin-dong, Dongan-gu, Anyang-si, Gyeonggi-do, 431-756 (KR)

( * ) Notice: Subject to any disclaimer, the term of this patent is extended or adjusted under 35 U.S.C. 154(b) by 255 days.

(21) Appl. No.: 10/444,494

(22) Filed: May 23, 2003

(65) Prior Publication Data

US 2004/0175672 A1 Sep. 9, 2004

(30) Foreign Application Priority Data

Mar. 3, 2003 (KR) .................... 10-2003-0013073

(51) Int. Cl.
*A61C 11/00* (2006.01)

(52) U.S. Cl. .................... 433/60; 433/61; 433/64

(58) Field of Classification Search ............ 433/54, 433/57, 58, 60, 61, 64; 403/90
See application file for complete search history.

(56) References Cited

U.S. PATENT DOCUMENTS 2,433,594 A * 12/1947 Calo .................... 84/421
4,382,787 A   5/1983 Huffman
4,533,323 A * 8/1985 Huffman .................... 433/60
4,673,376 A * 6/1987 Fender .................... 464/158
4,797,097 A * 1/1989 Cohn .................... 433/64
5,425,636 A * 6/1995 Ghim .................... 433/64
6,450,809 B1 * 9/2002 Iverson .................... 433/64

* cited by examiner

*Primary Examiner*—Todd E. Manahan
(74) *Attorney, Agent, or Firm*—Kin-Wah Tong, Esq.; Patterson & Sheridan, LLP

(57) ABSTRACT

Disclosed is a dental model articulator to connect the upper and the lower dental model casts. A mounting member is respectively mounted on each upper and lower cast, and a pair of elastic connecting members are connected to the mounting members. A vertical bar of the elastic connecting member has an S-type serpentine portion. The cast can smoothly move to the front, rear, left and right side by the S-type serpentine portion. A fastening member connects and disconnects the elastic connecting member and the mounting member by fastening a socket of the mounting member. A pivot member connects each elastic connecting member enabling to be pivoted. Whereby, the connecting ball of the elastic connecting member and the socket of the mounting member are connected by the fastening member, therefore the connecting ball can be connected to and disconnected from the socket.

5 Claims, 7 Drawing Sheets

DENTAL MODEL ARTICULATOR

TECHNICAL FIELD

This application claims priority to co-pending Republic of Korea Patent Application No. 2003-13073, filed Mar. 3, 2003, which is hereby incorporated by reference in its entirety.

The present invention relates to a dental model articulator, and more particularly to a dental model articulator in which an elastic connecting member is detachably connected to a mounting member by a fastening member and the mounting member is detachably connected to a dental model cast by a fastening member, the elastic connecting member being provided with a serpentine portion, thereby enabling to be moved to the front, rear, left and right side.

BACKGROUND ART

A dental model articulator is a device to assist to process a prosthetic denture. Dental models of a patient having damaged teeth are mounted on casts, and then the casts are mounted on the articulator. Afterwards, the articulator simulates occlusal movement and masticatory movement of the dental models so that the dental models are well operated instead of the damaged teeth when they are mounted on the real corresponding damaged teeth.

As an example of a dental model articulator, the dental model articulator is disclosed in U.S. Pat. No. 4,382,787, as shown in FIG. 7.

In the dental model articulator 10, the mounting means 22, 24 are mounted on the slot 44 formed on the dental model cast 12, 14, respectively. The mounting means 22, 24 are ball-connected to a pair of elastic brackets 10, 20, and each elastic bracket 10, 20 is pivotedly connected to each other.

The mounting means 22, 24 are fixedly mounted to the casts 12, 14 by applying a predetermined adhesive between the mounting means 12, 14 and the slot 44.

Further, the mounting means 22, 24 are fixedly connected to the brackets 10, 20 by applying a predetermined adhesive between the slot 44 formed on the mounting means 22, 24 and the connecting ball formed on the brackets 10, 20.

However, in this prior dental model articulator, an adhesive should be used to fixedly mount and connect the mounting means on/to the cast and the bracket respectively, thereby once the dental model articulator is mounted or connected on/to the cast, it can not be dismounted or disconnected.

Whereby, the connected position or the connected relationship between the mounting means and the cast and between the mounting and the bracket can not be changed.

Further, it is difficult and troublesome to mount the dental model articulator onto the dental model cast using an adhesive. Therefore, the technician needs to put great effort and labor as well as time to achieve the work repeatedly.

Further, once the dental model articulator is mounted on or connected to the cast, it can not be dismounted or disconnected. Therefore, it can not be used again, which causes waste of its materials.

Further, the brackets can not move well to the front, rear, left and right side, therefore the sufficient simulation for the real occlusal and masticatory movement can not be achieved.

DISCLOSURE OF INVENTION

Therefore, the present invention has been developed to solve the above-mentioned problems. It is an object of the present invention to provide a dental model articulator in which an elastic connecting member can be connected to and disconnected from an mounting member by connecting the elastic connecting member to the mounting member using an fastening member.

It is another object of the present invention to provide a dental model articulator in which a mounting member can be mounted on and dismounted from a cast by mounting the mounting member on the cast using an inserting member.

It is still another object of the present invention to provide a dental model articulator in which an vertical part of an elastic connecting member is provided with S-type serpentine portion so that a dental model cast can move easily to the front, rear, left and right side.

In order to achieve the above objects of the present invention, the present invention provides a dental model articulator including a mounting member each connected to a upper and a lower dental model casts, a pair of U-type elastic connecting members connected to the mounting member, and a pivot member which pivotedly connects the pair of elastic connecting members, the dental model articulator comprises a fastening member which is screwedly connected to the outer periphery surface of the mounting member and connects the mounting member to the elastic connecting member enabling to be disconnected.

The mounting member of the present invention includes a mounting plate formed with mounting projections, a mounting body which supports the mounting plate and is formed with first threads on the outer periphery surface thereof, and a cut-type socket integrally formed on the mounting body. The cut-type socket has a spherical conical portion on the inner bottom surface thereof, and the end portion thereof is spherically bent toward the center thereof.

The fastening member of the present invention is a hollowed-cylindrical type, and covers the outer periphery surfaces of the mounting body and the cut-type socket. Further, a plurality of projections are formed on the outer periphery surface of the fastening member, and second threads corresponding to the first threads are formed on the inner periphery surface. Herein, the first threads and the second threads are formed in taper-type, therefore the cut-type socket is gradually, strongly fastened by the rotation of the fastening member.

Further, the present invention provides a dental model articulator including a mounting member each connected to the upper and lower dental model cast, a pair of U-type elastic connecting members connected to the mounting member, and a pivot member which pivotedly connects the pair of elastic connecting members, the dental model articulator comprises, a mounting member having a mounting projection corresponding to the mounting recess formed on the cast and formed with an inserting space in center thereof, and an inserting member which is inserted in the mounting recess in a state that the mounting projection is inserted therein so that the mounting member is fixedly mounted on the cast enabling to be dismounted.

The inserting member of the present invention includes a triangle projection being inserted in the mounting projection and a supporting plate supporting the triangle projection.

The height $h_2$ of a portion, which is contacted to the supporting plate, in the triangle projection, is formed to be greater than the height $h_1$ of the inserting space formed in the mounting projection. Whereby, the mounting projection is outwardly bent when the mounting projection is fully forcedly inserted into the inserting member.

Further, the present invention provides a dental model articulator including a mounting member each connected to the upper and a lower dental model casts, a pair of U-type elastic connecting members connected to the mounting member, and a pivot member which pivotedly connects the pair of elastic connecting members, the dental model articulator comprises an elastic connecting member having more than one S-type serpentine portions in predetermined position so that the cast can move to the front, rear, left and right side.

Further, the present invention provides a dental model articulator including a mounting member each connected to the upper and a lower dental model casts, a pair of U-type elastic connecting members connected to the mounting member, and a pivot member which pivotedly connects the pair of elastic connecting members, the dental model articulator comprises a fastening member which is screwedly connected to the outer periphery surface of the mounting member and connects the mounting member to the elastic connecting member enabling to be disconnected, a mounting member having a mounting projection corresponding to the mounting recess formed on the cast and formed with a inserting space in center thereof, and an inserting member which is inserted into the mounting recess in a state that the inserting member is inserted in the mounting projection so that the mounting member is fixedly mounted on the cast enabling to be dismounted, and the elastic connecting member having more than one S-type serpentine portions in predetermined position so that the cast can move to the front, rear, left and right side.

BRIEF DESCRIPTION OF DRAWINGS

Other features and advantages of the present invention will become more apparent from the following description taken in connection with the accompanying drawings, wherein.

DESCRIPTION OF THE PREFERRED EMBODIMENT(S)

Hereinafter, the dental model articulator 100 according to the preferred embodiments of the present invention will be explained in detail referring to FIGS. 1 to 6.

Figure 1:
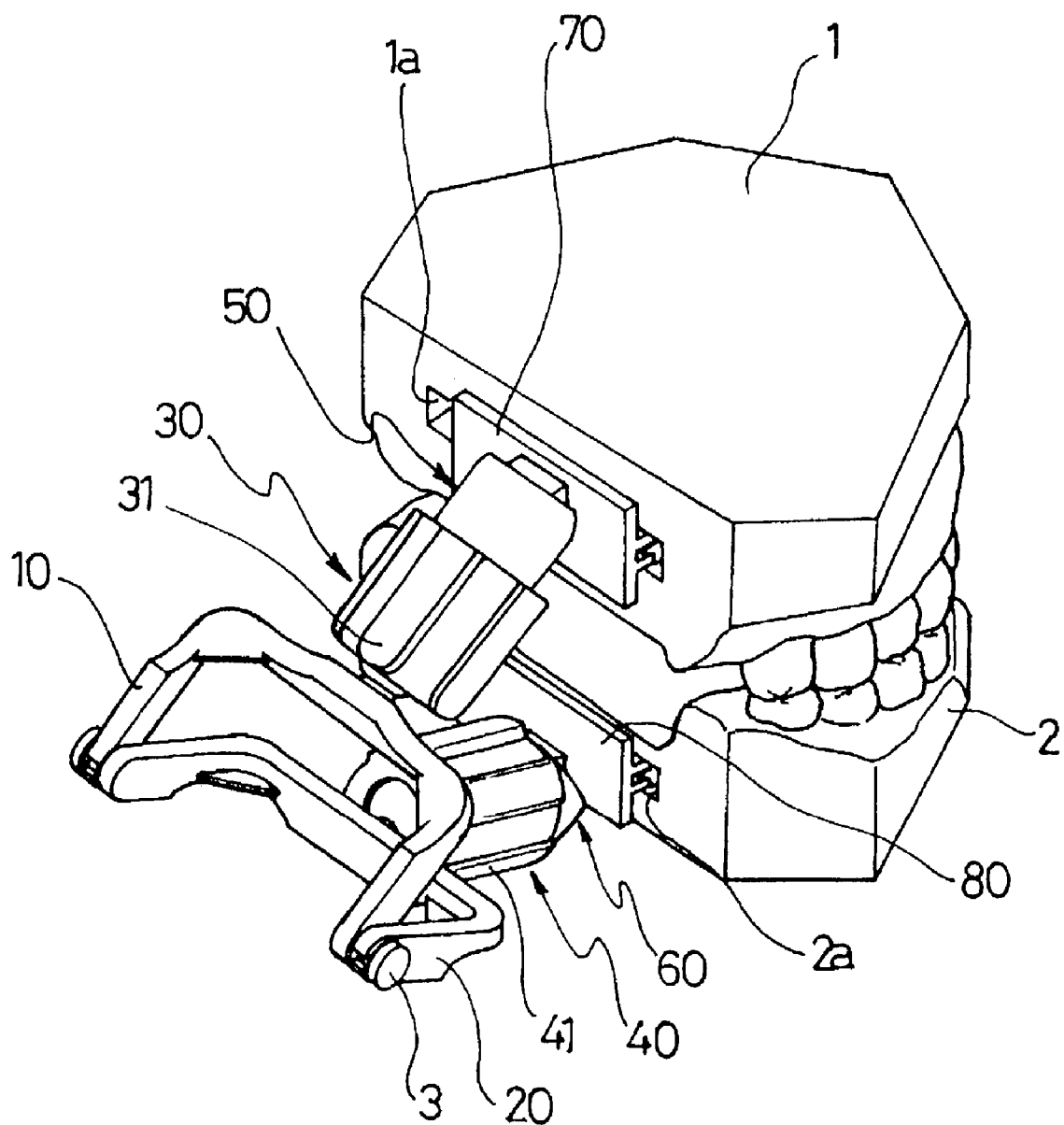
FIG. 1 is a schematic overall perspective view of the dental model articulator according to a preferred embodiment of the present invention, which is mounted on a upper and a lower dental model casts.

As shown in FIG. 1, in the dental model articulator 100 according to the preferred embodiment of the present invention, the mounting members 50, 60 are mounted on the upper and the lower dental model casts 1, 2 in a state in which the inserting members 70, 80 are inserted therein. A pair of elastic connecting members 10, 20 are connected to each mounting members 50, 60 by the fastening members 30, 40 respectively. Further, the free ends of the elastic connecting members 10, 20 are pivotedly connected to each other, therefore the casts 1, 2 can move to the front and rear side.

Figure 2:
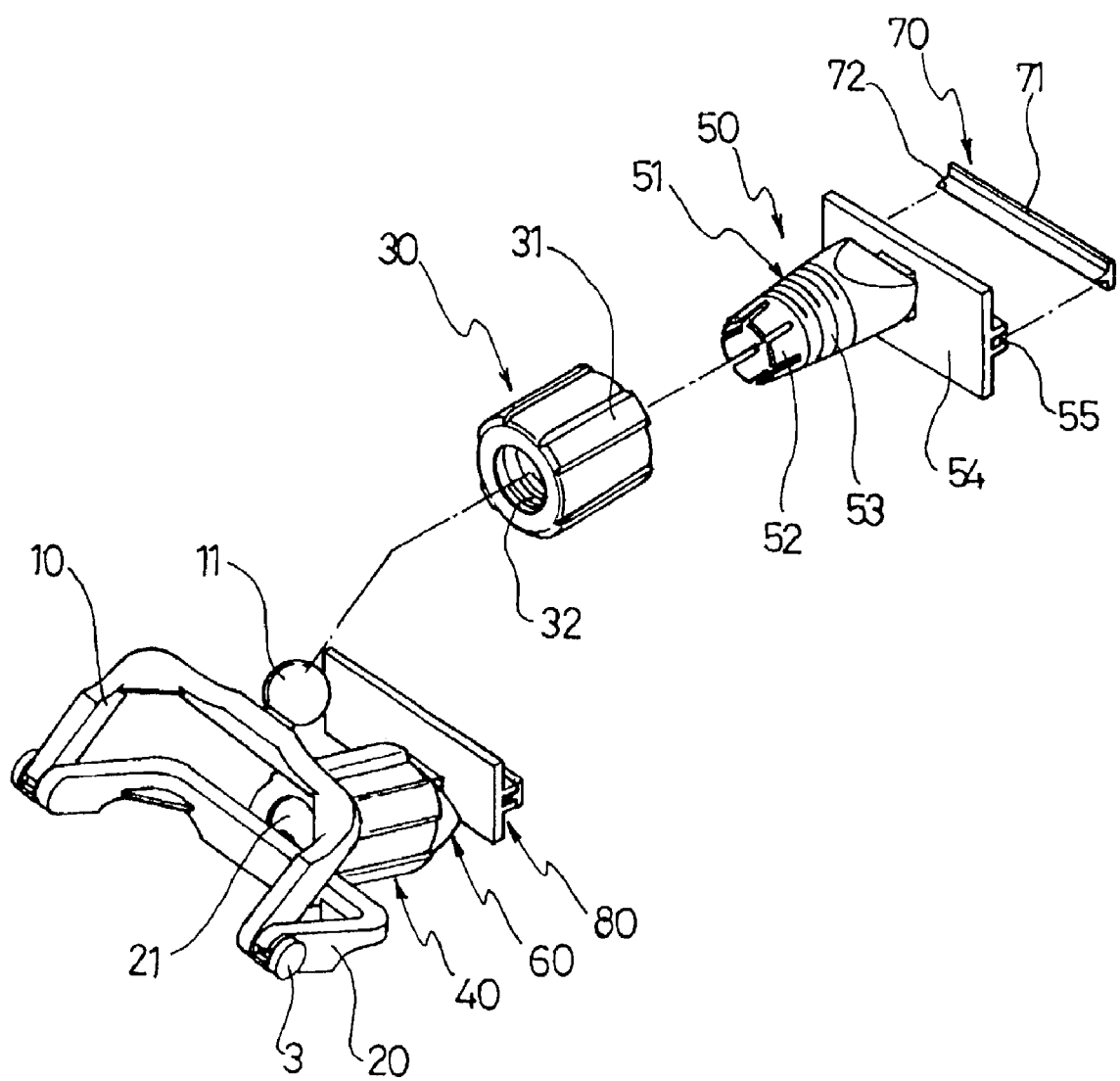
FIG. 2 is a broken perspective view of the dental model articulator in FIG. 2.
Figure 3:
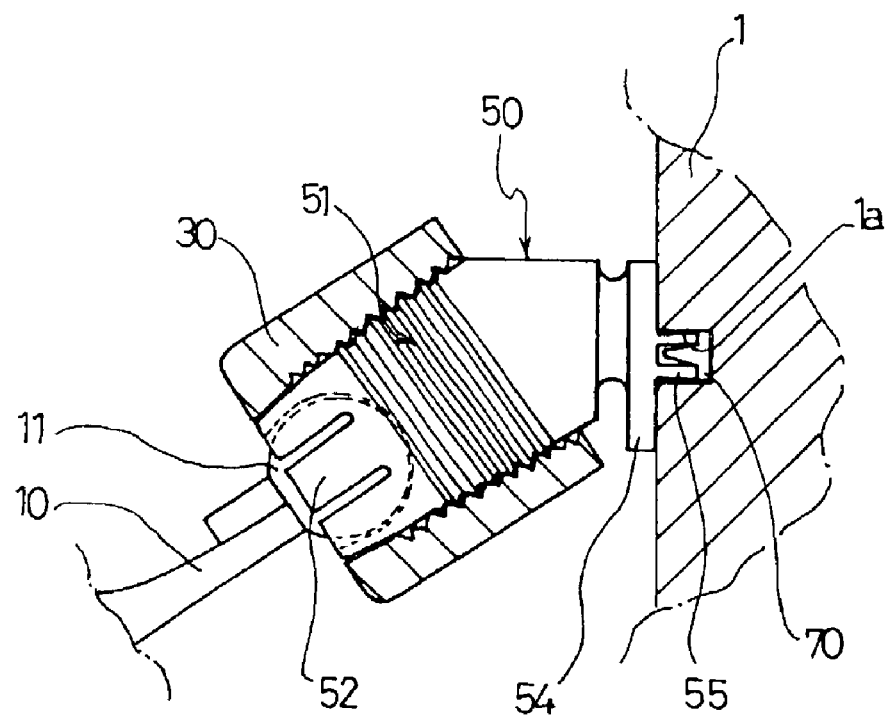
FIG. 3 is a partial cross sectional view showing a state in which the dental model articulator in FIG. 1 is mounted on a dental model cast.
Figure 4:
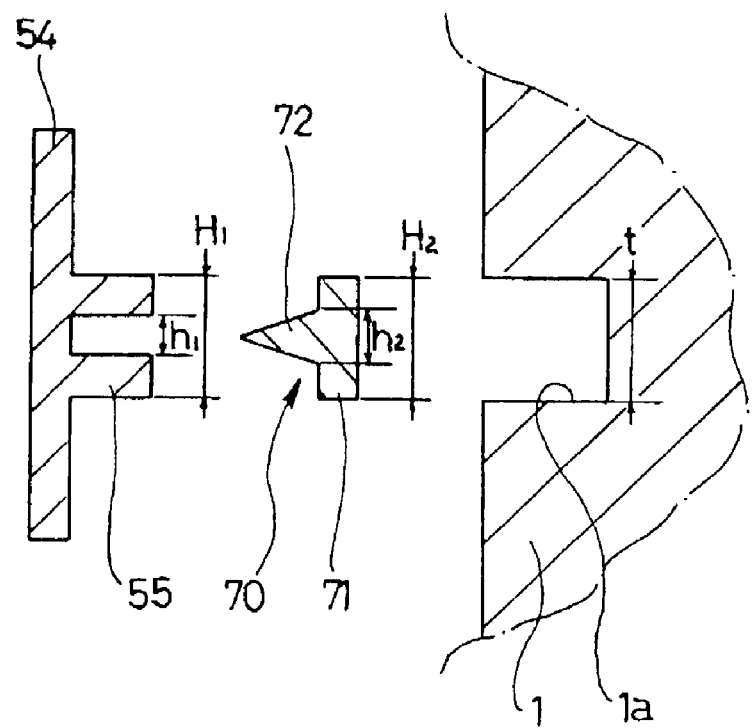
FIG. 4 is a partial cross sectional view showing a size relationship among the mounting plate and the inserting member of the articulator in FIG. 1 and the mounting recess of the cast.

Hereinafter, the dental model articulator 100 having above-mentioned structure will be explained in detail referring to FIGS. 2 to 4. Each structure of the upper part and the lower part of the dental model articulator 100 to be mounted to the upper and the lower dental model casts 1, 2 is the same as each other. Therefore, herein, the essential components related to the upper dental model cast 1 will be explained, and those of the lower dental model cast 2 will be omitted.

Preferably, the elastic connecting member 10 is made of predetermined elastic materials. The elastic connecting member 10 is formed in U-type. That is, U-type consists of two vertical bars 10a and one horizontal bar 10b. The connecting ball having a predetermined diameter is provided on the horizontal 10b as a connecting means against the mounting member 50. Further, a curved portion is formed on a predetermined position of each vertical bar 10b in order to be easily grapsed. The elastic connecting member 10 will be explained in more detail referring to FIGS. 5 and 5a in the future.

The mounting member 50 has the mounting plate 54 formed with the mounting projection 55, the mounting body 51 supporting the mounting plate 54 and the cut-type socket 52 receiving the connecting ball 11.

The mounting plate 54 is a rectangular plate. And, the mounting projection 55 is longitudinally formed in the intermediate of the one side surface of the plate 54, and the mounting body 51 is integrally formed on the other side surface of the plate 54. As shown in FIG. 4 in detail, the mounting projection 55 is formed in U-type having a conical portion in the center thereof, the height $H_1$ including each free ends is substantially the same as the thickness t of the mounting recess 1a formed in the cast 1. Further, the mounting projection 55 has a predetermined elasticity, therefore it can be bent in predetermined angle when an outer force is applied thereon.

The mounting body 51 is a cylindrical type. One portion thereof is formed with the first threads 53 on the outer periphery thereof and connected to the fastening member 30, and the other portions are integrally formed with the mounting plate 54.

The cut-type socket 52 is a thinned-hollowed-cylindrical type, and the total length thereof is substantially the same as the diameter of the connecting ball 11. Further, a spherical conical portion (not shown) is formed on the inner bottom surface of the cut-type socket 52 in order to correspond to a portion of the connecting ball 11. Further, the cut-type socket 52 has plural cutting portions, and the free ends thereof are somewhat spherically bent toward the center thereof in order to be strongly connected to the connecting ball 11.

Whereby, when the connecting ball 11 is inserted into the cut-type socket 52, nearly whole surface thereof is covered with the cut-type socket 52. Further, when the cut-type socket 52 is fastened by the fastening member 30, the connecting ball 11 is fixedly safely connected to the cut-type socket 52.

The fastening member 30 is a hollowed-cylindrical type having a predetermined inner diameter through which the connecting ball 11 can pass. The fastening member 30 is formed so that the inner diameter of one end in which the connecting ball 11 is inserted is smaller than that of the other end. That is, it is a taper type. Further, the second threads 32 corresponding to the first threads 53 formed on the outer periphery surface of the mounting body 51 of the mounting member 50 are formed on the whole inner periphery surface of the fastening member 30.

Whereby, if the fastening member 30 is screwedly connected to the mounting body 51 of the mounting member 50 during rotation thereof, the cut portions of the cut-type socket 52 gradually cover and force the outer periphery of the connecting ball 11. Therefore, when the fastening member 30 is fully fastened, the whole spherical surface of the connecting ball 11 is fully fixed by the conical portion formed on the bottom surface of the cut-type socket 52 and by the cut portions. This causes the same effect as when the connecting ball is attached to the socket by an adhesive.

If the elastic connecting member 10 is not preferably connected to the mounting 50, one releases the fastening member 30 and then curtails the connecting force between the cut-type socket 52 and the connecting ball 11. Afterward, one makes the elastic connecting member 10 to be preferably connected to the mounting 50 and fastens the fastening member 30 again.

The inserting member 70 has the triangle projection 72 inserted into the conical portion of the mounting projection 55 and the supporting plate 71 supporting the triangle projection 72, and the triangle projection 72 is integrally formed with the supporting plate 71. The height $h_2$ of a portion, which is contacted to the supporting plate 71 in the triangle projection 72, is formed to be somewhat greater than the height $h_1$ of the inserting space of the mounting projection 55. Further, the height $H_2$ of the supporting plate 71 is substantially the same as the thickness t of the mounting recess 1a formed in the cast 1. Whereby, when the mounting projection 55 is inserted into the mounting recess 1a of the cast 1 in a state where the inserting member 70 is not fully inserted into the mounting projection 55 of the mounting plate 54, the inserting member 70 is fully inserted into the mounting member 50. At this time, the portion $h_2$ of the triangle projection 72, which is formed to be greater than the height $h_1$ of the inserting space of the mounting projection 55, outwardly forces the mounting projection 55. Whereby, the outer surface of the mounting projection 55 is forcedly, closely contacted to the mounting recess 1a of the cast 1.

If one wants to disconnect the mounting member 50 from the cast 1, one inserts a predetermined slender tool, like a pin, in the mounting recess 1a and then raises the edge of the inserting member 70. Thereby, the inserting member 70 and the mounting projection 55 are simultaneously disconnected from the mounting recess 1a.

Figure 5:
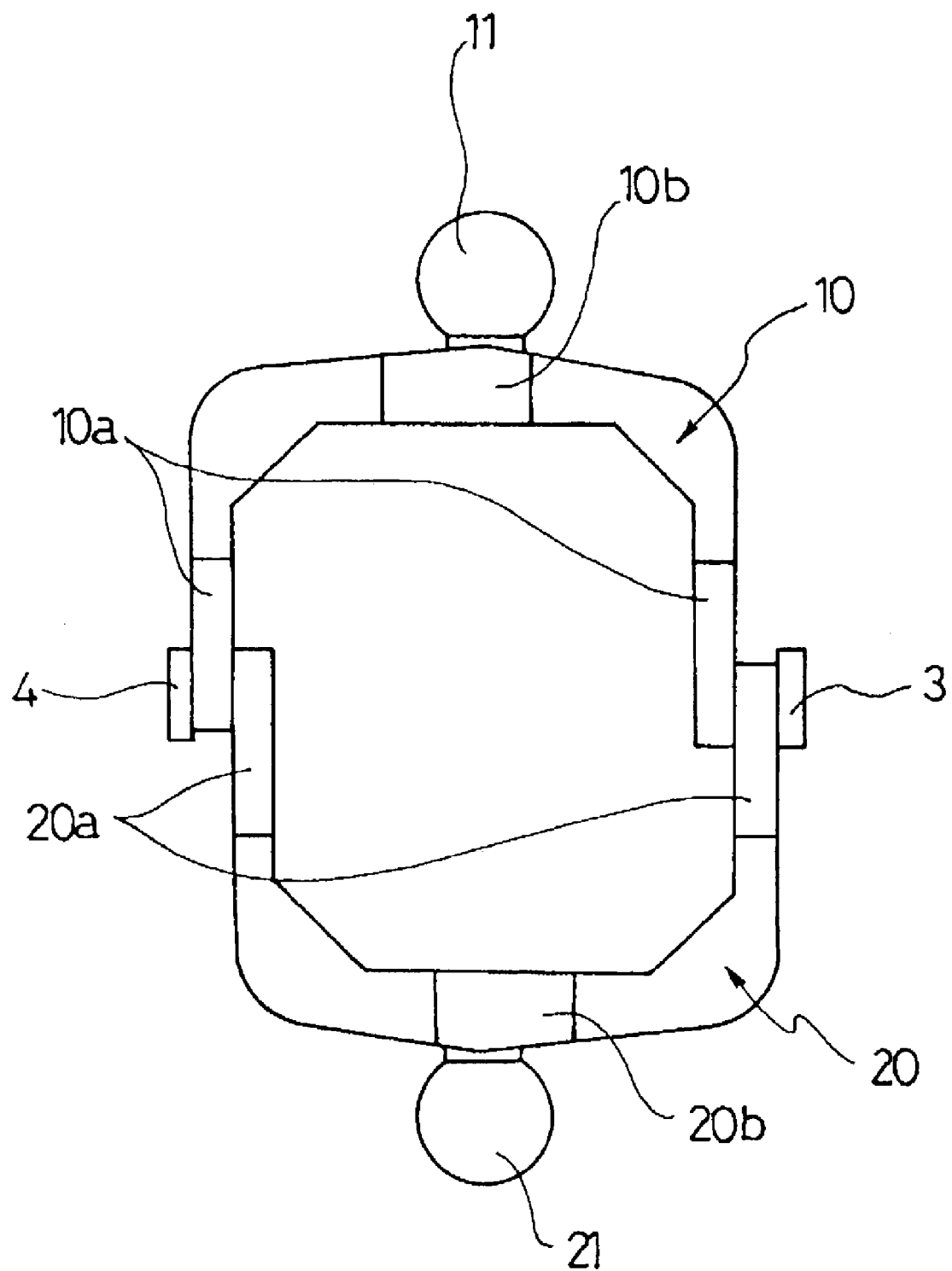
FIG. 5 is a plan view of an elastic connecting member of the dental model articulator in FIG. 1.
Figure 5A:
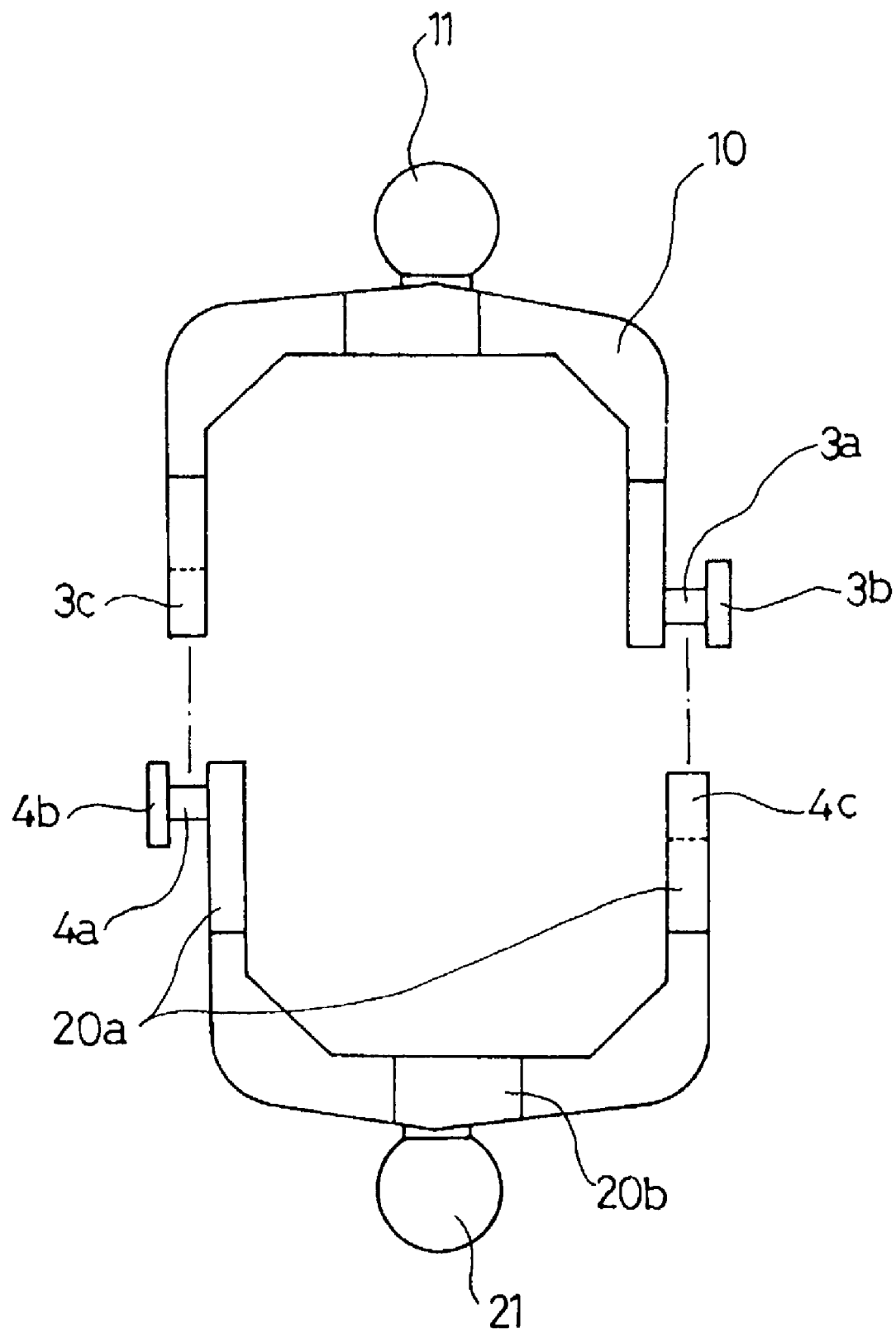
FIG. 5a is a broken view of the elastic connecting member in FIG. 4.
Figure 6:
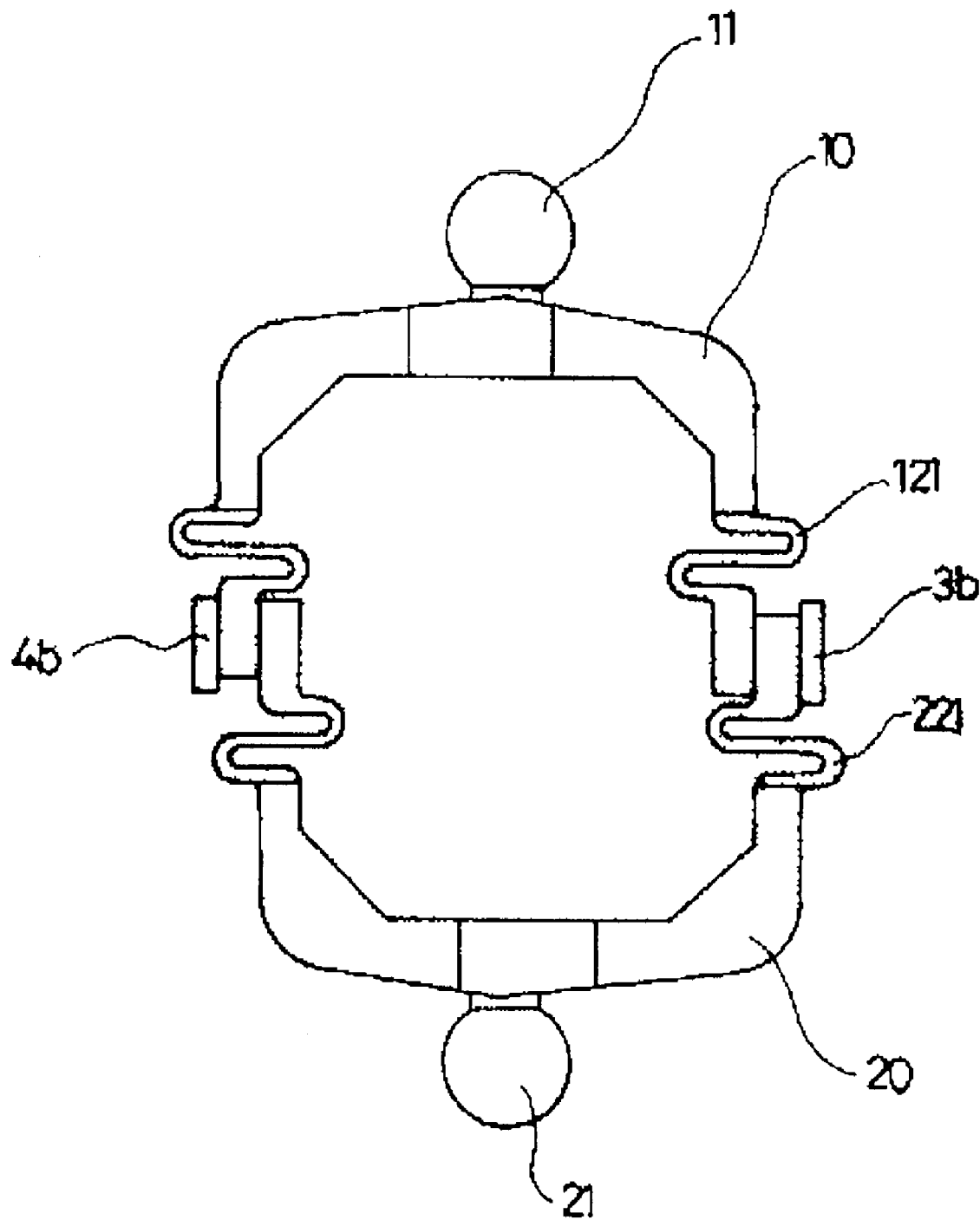
FIG. 6 is a plan view of an elastic connecting view according to another preferred embodiment of the present invention.
Figure 7:
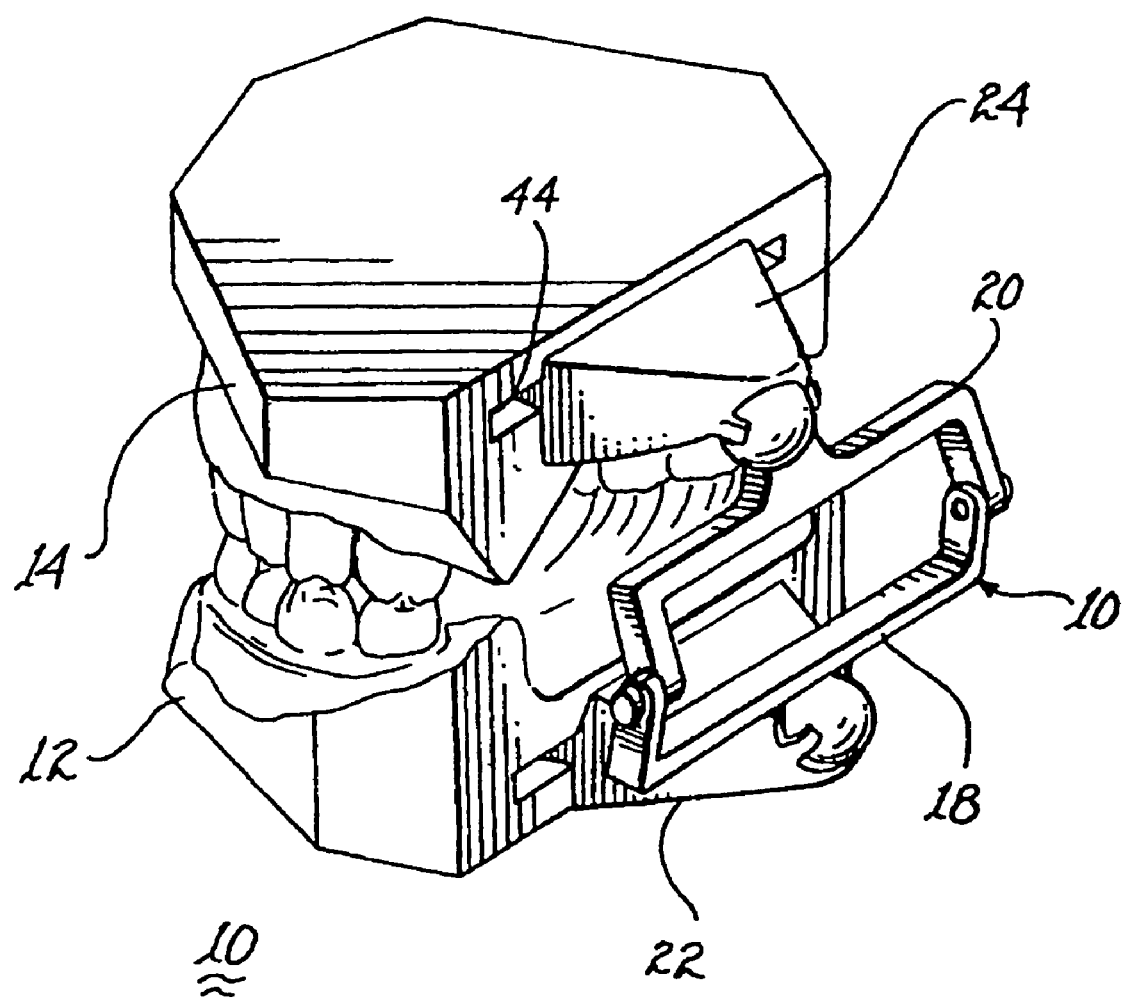
FIG. 7 is a schematic overall perspective view of the prior dental model articulator, which is mounted on the upper and the lower dental model cast.

Next, the elastic connecting members 10, 20 will be explained in detail referring to FIGS. 5 and 5a.

The elastic connecting members 10, 20, as described above, are in U-type and also in mirror type. That is, two vertical bars 10a are integrally connected to one horizontal bar 10b. The connecting balls 11, 21 are integrally formed in the intermediate of the horizontal bar 10b. Further, T-type pivot members 3, 4 are formed on the outer side of the end of the vertical bars 10a, 20a respectively. Preferably, the vertical portion 3a, 4a of the T-type pivot member 3, 4 are cylindrical type, and the horizontal portions 3b, 4b are circular plate type. Further, the C-type pivot recesses 3c, 4c for rotatably receiving the cylindrical vertical portions 3a, 4a of the T-type pivot members 3, 4 are formed on the outer side of the end of the other vertical bars 10a, 20a respectively.

The vertical portion 3a of the T-type pivot member 3 of the elastic connecting member 10 is inserted onto the pivot recess 4c of the elastic connecting member 20. Also, the vertical portion 4a of the T-type pivot member 4 of the elastic connecting member 20 is inserted into the pivot recess 3c of the elastic connecting member 10. Whereby, the elastic connecting members 10, 20 are connected to each other so that they are pivotedly rotated against the pivot members 3, 4.

Next, another preferred embodiment of the elastic connecting member of the present invention will be explained. Since the structure of the elastic connecting member according to another preferred embodiment is substantially the same as that of the elastic connecting member described above, the reference numerals for the same components are omitted.

The structure of the horizontal bar of each connecting member 10, 20 and the pivot member is the same as that of the embodiment described above. However, the S-type serpentine portions 121, 221 are provided on the vertical bar respectively. Whereby, the dental model cast can move to the front, rear, left and right side, therefore occlusion of the real teeth and the up and down motion, the left and right motion and the front and rear motion can be nearly, perfectly simulated.

While the present invention has been particularly shown and described with reference to particular embodiments thereof, it will be understood by those skilled in the art that various changes in form and details may be effected therein without departing from the spirit and scope of the invention as defined by the appended claims.

According to the dental model articulator of the present invention, the mounting member can be connected to and disconnected from the dental model cast. Further, since the connecting ball of the elastic connecting member and the socket of the mounting member are connected by the fastening member, they can be connected to and disconnected from each other easily.

Whereby, the once used dental model articulator can be reused, therefore it is not required to manufacture the dental model articulator for each cast, which can save the materials required to manufacture the dental model articulator.

Further, since the elastic connecting member and the mounting member are connected to and disconnected from each other by the fastening member, the connecting relationship theirbetween can be changed.

Further, since no adhesive is used to connect the elastic connecting member to the mounting member and to connect the mounting member to the cast, the manufacturing time and labor required for the dental model articulator can be saved.

Further, since the elastic connecting member is provided with S-type serpentine portion, the cast can achieve the front, rear, left and right movement. Thereby, the cast mounted on the dental model articulator can simulate the real dental movement.

The invention claimed is:

1. A dental model articulator including a mounting member each connected to a upper and a lower dental model casts, a pair of U-type elastic connecting members connected to said mounting member, and a pivot member which pivotedly connects said pair of elastic connecting members, said dental model articulator comprises:
   a mounting member having a mounting projection corresponding to a mounting recess formed on said cast and formed with an inserting space on the center thereof; and
   an inserting member inserted into said mounting recess in a state where said inserting member is inserted into said mounting projection so that said mounting member is fixedly mounted on said cast enabling to be disconnected.

2. The dental model articulator as claimed in claim 1, wherein said inserting member is provided with a triangle projection being inserted into said mounting projection and a supporting plate supporting said triangle projection, and wherein the height $h_2$ of the portion, which is contacted to said supporting plate, in said triangle projection, is formed to be greater than the height $h_1$ of the inserting space formed on said mounting projection, so that said mounting projection is outwardly bent when said inserting projection is fully forcedly inserted into said mounting projection.

3. One of the dental model articulators as claimed in claims 1 or 2, wherein said elastic connecting member is provided with a serpentine portion on its predetermined position so that it is easily held.

4. A dental model articulator including a mounting member each connected to a upper and a lower dental model casts, a pair of U-type elastic connecting members connected to said mounting member, and a pivot member which pivotedly connects said pair of elastic connecting members, said dental model articulator comprises:
   an elastic connecting member provided with plural S-type serpentine portions on a predetermined position thereof so that said cast moves to the front, rear, left and right side.

5. A dental model articulator including a mounting member each connected to a upper and a lower dental model casts, a pair of U-type elastic connecting members connected to said mounting member, and a pivot member which pivotedly connects said pair of elastic connecting members, said dental model articulator comprises:
   a fastening member which is screwedly connected to the outer periphery surface of said mounting member and connects said mounting member to said elastic connecting member enabling to be disconnected;
   a mounting member having a mounting projection corresponding to a mounting recess formed on said cast and formed with an inserting space on the center thereof;
   an inserting member to be inserted in said mounting recess in a state where said inserting member is inserted into said mounting projection so that said mounting member is fixedly mounted on said cast enabling to be disconnected; and
   an elastic connecting member provided with plural S-type serpentine portions on predetermined position so that said cast can move to the front, rear, left and right side.

* * * * *